US00PP24745P2

(12) United States Plant Patent
Vitten et al.

(10) Patent No.: US PP24,745 P2
(45) Date of Patent: Aug. 12, 2014

(54) STRAWBERRY PLANT NAMED 'DRISSTRAWTHIRTYFIVE'

(50) Latin Name: *Fragaria×ananassa*
Varietal Denomination: DrisStrawThirtyFive

(71) Applicant: Driscoll Strawberry Associates, Inc., Watsonville, CA (US)

(72) Inventors: Matthias D. Vitten, Aptos, CA (US); Carlos D. Fear, West Malling (GB); Abigail Johnson, Rochester (GB)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 45 days.

(21) Appl. No.: 13/815,229

(22) Filed: Feb. 12, 2013

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of strawberry plant named 'DrisStrawThirtyFive' particularly characterized by high yield, long shelf life, and medium red berries with sweet flavor, is disclosed.

2 Drawing Sheets

Genus and species: *Fragaria×ananassa.*
Variety denomination: 'DrisStrawThirtyFive'.

BACKGROUND OF THE NEW PLANT

The present invention relates to a new and distinct strawberry variety designated 'DrisStrawThirtyFive' and botanically known as *Fragaria×ananassa*. This new strawberry variety was discovered in Kent, United Kingdom in May 2008 and originated from a cross between the proprietary female parent 'KGEM 0148' (unpatented) and the proprietary male parent 'KGEM 0175' (unpatented). A single plant was selected for asexual propagation via tissue culture and vegetative cuttings in Kent, United Kingdom.

'DrisStrawThirtyFive' underwent further testing in Kent, United Kingdom for five years (2008-2012). The present invention has been found to retain its distinctive characteristics through successive asexual propagations via stolons and tissue culture.

Plant Breeder's Rights for this variety have not been applied for. 'DrisStrawThirtyFive' has not been made publicly available or sold more than one year prior to the filing date of this application.

SUMMARY OF THE INVENTION

The following are the most outstanding and distinguishing characteristics of this new cultivar when grown under normal horticultural practices in Kent, United Kingdom.

1. High yield;
2. Long shelf life; and
3. Medium red berries with sweet flavor.

DESCRIPTION OF THE PHOTOGRAPH

The accompanying color photographs show typical specimens of the new variety at various stages of development. The colors shown are as true as can be reasonably obtained by conventional photographic procedures. The photographs were taken from eight to ten-month-old plants.

DESCRIPTION OF THE NEW VARIETY

Figure 1:
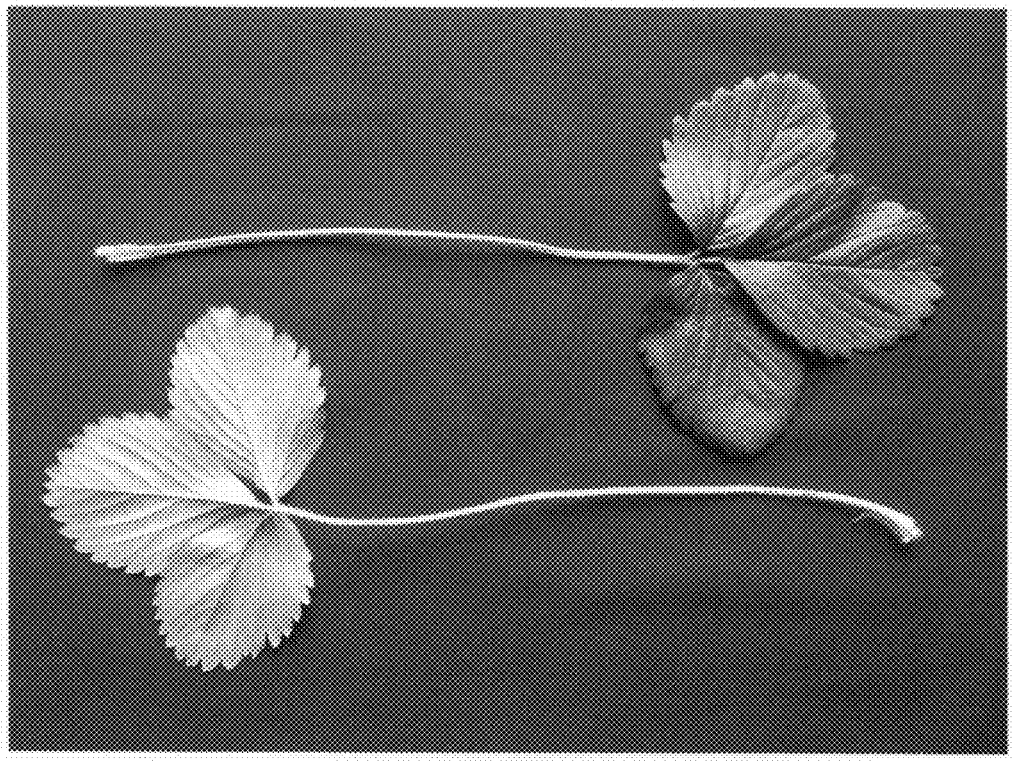
FIG. 1 shows upper and lower surfaces of the leaves of the plant with three leaflets.
Figure 2:
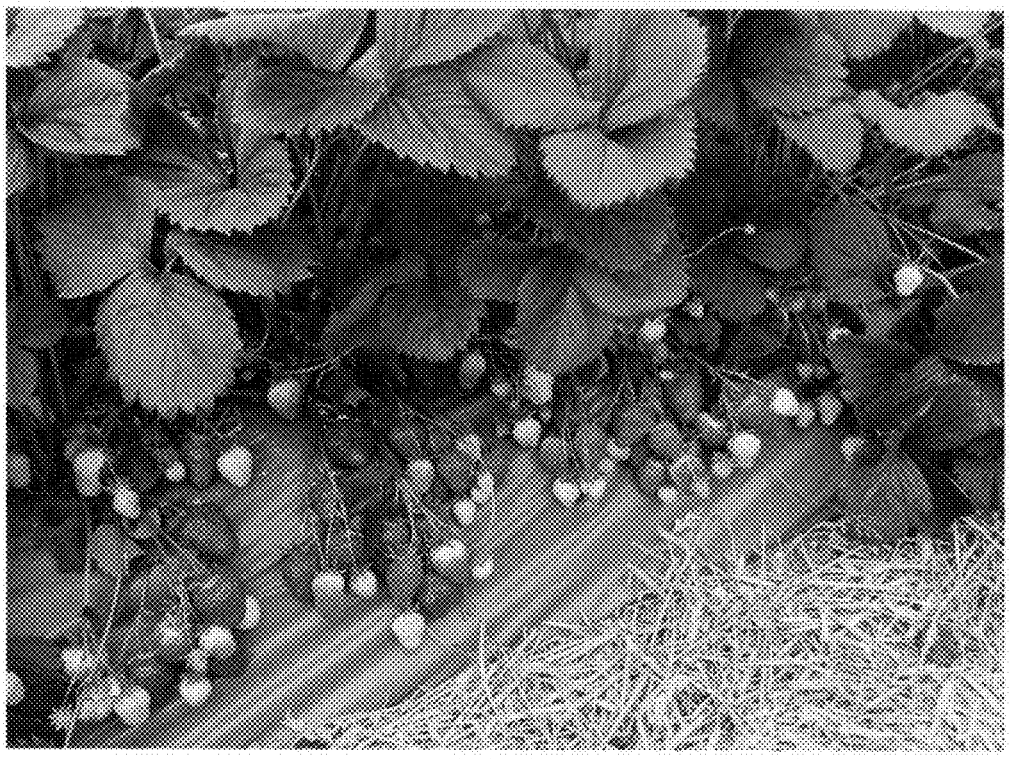
FIG. 2 shows whole plants with fruit.
Figure 3:
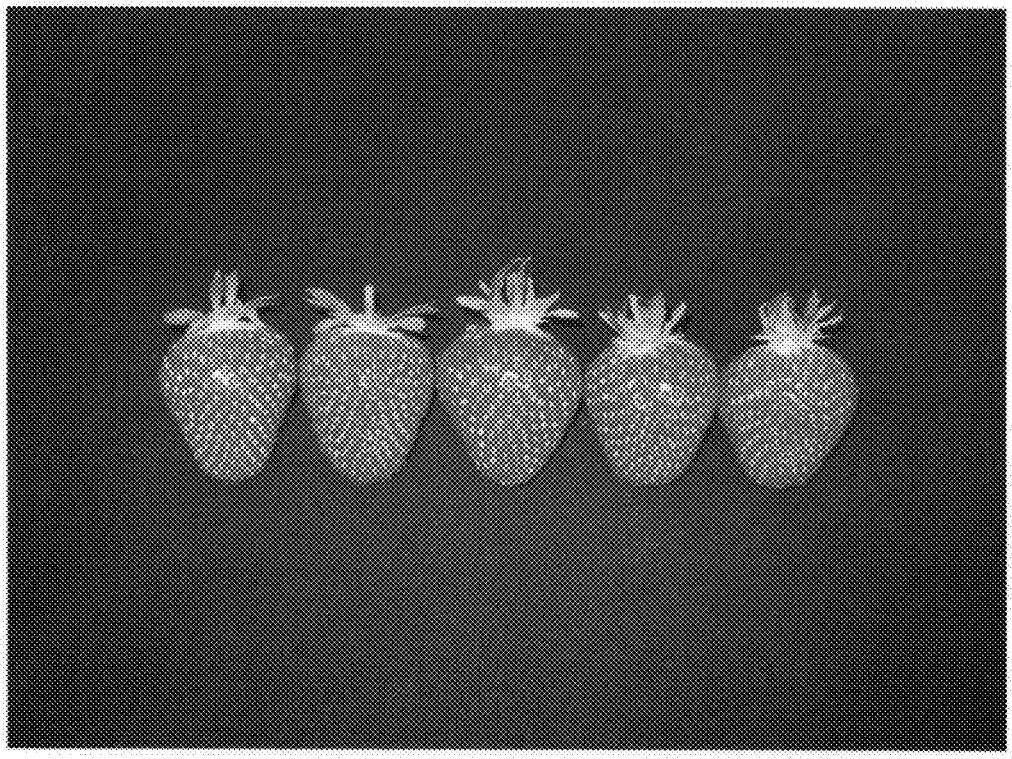
FIG. 3 shows the whole fruit.
Figure 4:
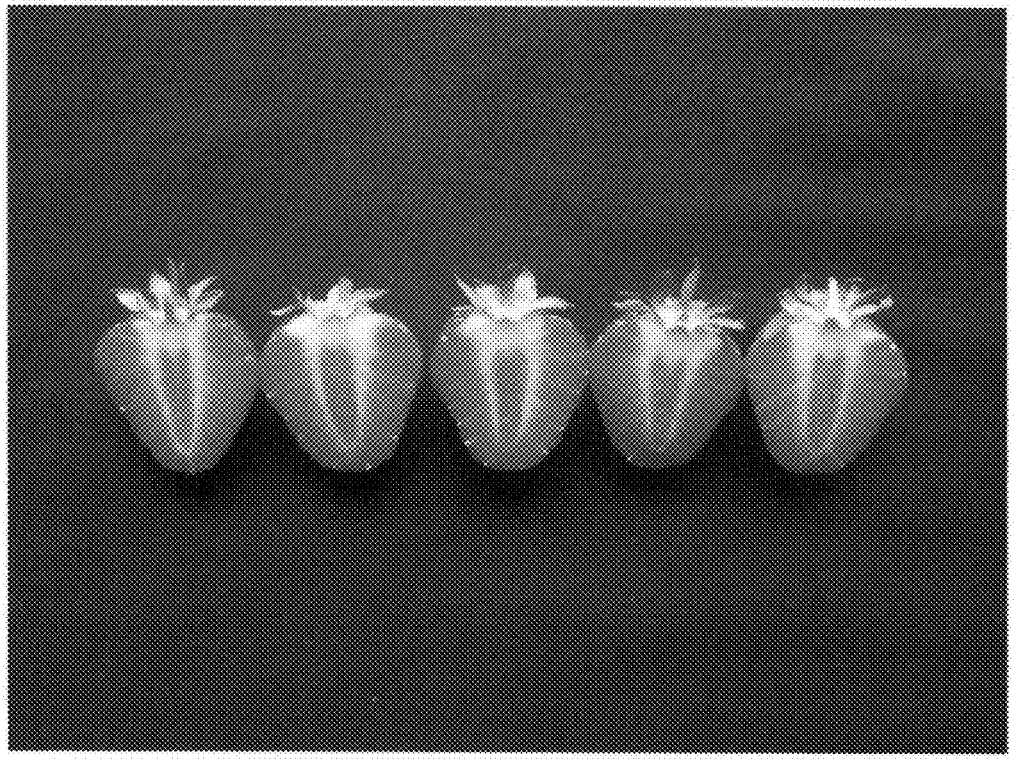
FIG. 4 shows the fruit in longitudinal cross-section.

The following detailed descriptions set forth the distinctive characteristics of 'DrisStrawThirtyFive'. The data which define these characteristics is based on observations taken in Kent, United. Kingdom from 2008 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyFive' has not been observed under all possible environmental conditions. The botanical description of 'DrisStrawThirtyFive' was taken from eight to ten month-old plants. Color references are primarily to The R.H.S. Colour Chart of The Royal Horticultural Society of London (R.H.S.) (2007 edition). Descriptive terminology follows the Plant Identification Terminology, An Illustrated Glossary, 2$^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtyFive'.

Parentage:

*Female parent.*—The proprietary variety 'KGEM 0148' (unpatented).

*Male parent*.—The proprietary variety 'KGEM 0175' (unpatented).

Plant:

*Height*.—44.4 cm.

*Diameter*.—55.6 cm.

*Number of crowns/plant*.—3.

*Habit*.—Upright.

*Density of individual plant*.—Medium.

*Vigor* (*health and hardiness of plant*).—Strong.

Terminal Leaflets:

*Size*.—Medium. Length: 10.0 cm. Width: 8.36 cm. Length/width ratio: 1.2 (Longer than broad).

*Number of teeth/terminal leaflet*.—23.

*Shape of teeth*.—Acute to serrate.

*Color*.—Upper surface: RHS N137A (Dark green). Lower surface: RHS 138B (Medium green).

*Shape in cross section*.—Slightly concave.

*Blistering*.—Medium.

*Glossiness*.—Medium.

*Number of leaflets*.—Three only.

*Shape*.—Orbicular.

*Base shape*.—Acute.

*Apex descriptor*.—Complex.

*Variegation*.—Absent.

*Margin*.—Serrate.

*Margin profile*.—Revolute (margins rolled backwards).

Petiole:

*Length*.—Long; 37.5 cm.

*Diameter*.—5.88 mm.

*Pubescence*.—Sparse.

*Pose of hairs*.—Slightly upwards.

*Color*.—RHS 144B (Medium yellow-green).

*Bracts*.—Absent.

Petiolule:

*Length*.—9.58 mm.

*Diameter*.—2.61 mm.

*Color*.—RHS 144C (Light yellow-green).

Stipule:

*Length*.—4.05 mm.

*Width*.—8.60 mm.

*Pubescence*.—Sparse.

*Stipule anthocyanin coloration*.—Absent or very weak; RHS 145A (Light yellow-green).

Stolon:

*Number*.—Many.

*Average number of daughter plants per plant*.—35.

*Anthocyanin coloration*.—Absent or very weak; RHS N144A (Light yellow-green).

*Diameter at bract*.—3.54 mm.

*Thickness*.—Medium.

*Pubescence*.—Sparse.

Inflorescence:

*Position relative to foliage*.—Above.

*Number of flowers*.—Medium.

*Time of flowering* (*50% of plants at first flower*).—Medium.

*Flower size*.—Small.

*Diameter*.—30.71 mm.

*Petals*.—Shape: Orbicular. Apex: Rounded. Base: Concavo-convex. Margin: Entire. Spacing: Free. Length: 13.52 mm. Width: 11.83 mm. Length/width ratio: 1.1 (Slightly longer than broad). Petal number per flower: 6. Color (upper surface): RHS 155C (White).

*Calyx*.—Diameter: 23.98 mm. Diameter relative to corolla: Smaller. Inner calyx diameter relative to outer: Same size. Insertion of calyx: Level. Pose of calyx segments: Spreading to outwards. Size of calyx in relation to fruit: Slightly smaller. Adherence of calyx: Medium.

*Sepal*.—Shape: Elliptical. Apex: Truncate. Margin: Entire. Length: 8.57 mm. Width: 4.25 mm. Sepal number per flower: 6.

*Receptacle color*.—RHS 151B (Medium yellow-green).

*Stamen*.—Present. Anther color: RHS 153C (Medium yellow-green).

*Pedicel*.—Attitude of hairs: Slightly upwards.

Fruiting truss:

*Length*.—*Medium;* 29.8 cm.

*Diameter at base of truss*.—4.90 mm.

*Number of berries per fruiting truss*.—5.

*Attitude at first picking*.—Erect.

*Color at base of truss*.—RHS 144B (Medium yellow-green).

Fruit:

*Relative fruit size*.—Medium.

*Length*.—40.25 mm.

*Width*.—37.04 mm.

*Length/width ratio*.—1.1 (Longer than broad).

*Fruit hollow length*.—31.63 mm.

*Fruit hollow width*.—11.65 mm.

*Fruit hollow length/width ratio*.—2.7.

*Fruit hollow center* (*cavity*).—Small.

*Weight* (*per individual berry*).—18.6 g.

*Predominant fruit shape*.—Conical.

*Difference in shape between primary and secondary fruits*.—None or very slight.

*Evenness of fruit surface*.—Slightly uneven.

*Fruit skin color*.—RHS 42A (Medium red).

*Evenness of fruit color*.—Strongly uneven.

*Fruit glossiness*.—Strong.

*Achenes*.—Insertion of achenes: Level with surface. Coloration (both sunward and shaded sides of berry): RHS 172B (Medium greyed-orange). Number per berry: 376.0. Weight (weight of achenes divided by total # seed): 0.0006 g. Width of band without achenes: Absent or very narrow.

*Firmness of flesh* (*when fully ripe*).—Medium.

*Color of flesh* (*excluding core*).—RHS 44C (Medium red).

*Color of core*.—RHS 33B (Medium orange-red).

*Evenness of flesh color*.—Slightly uneven.

*Distribution of flesh color*.—Marginal and central.

*Sweetness*.—Medium.

*Acidity*.—Weak.

*Texture when tasted*.—Fine.

*Type of bearing*.—Not everbearing — not remontant.

*Grams of fruit/plant*.—1250.0 g.

*Harvest interval*.—Mid May to mid July.

*Harvest maturity*.—Late.

Disease and pest resistance: None observed.

Reaction to stress: None observed.

COMPARISON WITH PARENTAL AND COMMERCIAL VARIETIES

When 'DrisStrawThirtyFive' is compared to the female parent plant 'KGEM 0148' (unpatented), 'DrisStrawThirtyFive' has higher yields, better shelf life, and better flavor than 'KGEM 0148'.

When 'DrisStrawThirtyFive' is compared to the male parent plant 'KGEM 0175' (unpatented), 'DrisStrawThirtyFive' has higher yields, better shelf life, better flavor, and better resistance to Verticillium wilt than 'KGEM 0175'.

When 'DrisStrawThirtyFive' is compared to the commercial variety 'Sonata' (U.S. Plant Pat. No. 18,000), 'DrisStrawThirtyFive' has leaves with an acute base, freely spaced, orbicular shaped petals, and a medium flowering time, whereas 'Sonata' has leaves with an obtuse to rounded base, overlapping, broadly ovate shaped petals and an early flowering time. Additionally, 'DrisStrawThirtyFive' has medium red berries with a small hollow center, whereas 'Sonata' has light red berries with an absent or weakly expressed hollow center.

We claim:

1. A new and distinct variety of strawberry plant named 'DrisStrawThirtyFive' as described and shown herein.

* * * * *